United States Patent [19]

Wilder et al.

[11] Patent Number: 4,562,832

[45] Date of Patent: Jan. 7, 1986

[54] MEDICAL INSTRUMENT AND LIGHT PIPE ILLUMINATION ASSEMBLY

[76] Inventors: Joseph R. Wilder, 151 W. 86th St., Apt. 9D, New York, N.Y. 10024; Franklin G. Reick, 228 West Pl., Westwood, N.J. 07675

[21] Appl. No.: 612,149

[22] Filed: May 21, 1984

[51] Int. Cl.⁴ .......................... A61B 1/06; A61B 17/02
[52] U.S. Cl. .......................... 128/20; 128/18; 128/303 R; 362/32; 138/DIG. 8
[58] Field of Search ............... 128/20, 6, 11, 16, 18, 128/303 R; 362/32; 433/29; 138/DIG. 8

[56] References Cited

U.S. PATENT DOCUMENTS

| | | | |
|---|---|---|---|
| 3,592,199 | 7/1971 | Ostensen | 128/6 |
| 3,626,471 | 12/1971 | Florin | 128/20 |
| 3,641,332 | 2/1972 | Reick et al. | 362/32 |
| 3,729,006 | 4/1973 | Wilder et al. | 128/303 R |
| 3,733,481 | 5/1973 | Kuyt | 362/32 |
| 3,796,214 | 3/1974 | Davis | 128/20 |
| 3,851,642 | 12/1974 | McDonald | 128/18 |
| 4,156,424 | 5/1979 | Burgin | 128/20 X |

Primary Examiner—William H. Grieb
Attorney, Agent, or Firm—Michael Ebert

[57] ABSTRACT

A disposable medical instrument and light pipe illumination assembly fabricated of synthetic plastic material. When put to use, the instrument, such as a surgical retractor, assumes a position at which its operative section lies adjacent the field of medical interest, such as a body cavity or surgical site. Joined to the instrument is a short flexible light pipe whose optical inlet end is coupled to a light source and whose optical outlet end is next to the operative section to project light into the field. The outlet end of the light pipe is sheathed in a bendable tubular neck having dead-soft characteristics whereby by bending the neck, the user is able to orient the outlet to direct the projected light toward a desired region in the field of interest.

5 Claims, 8 Drawing Figures

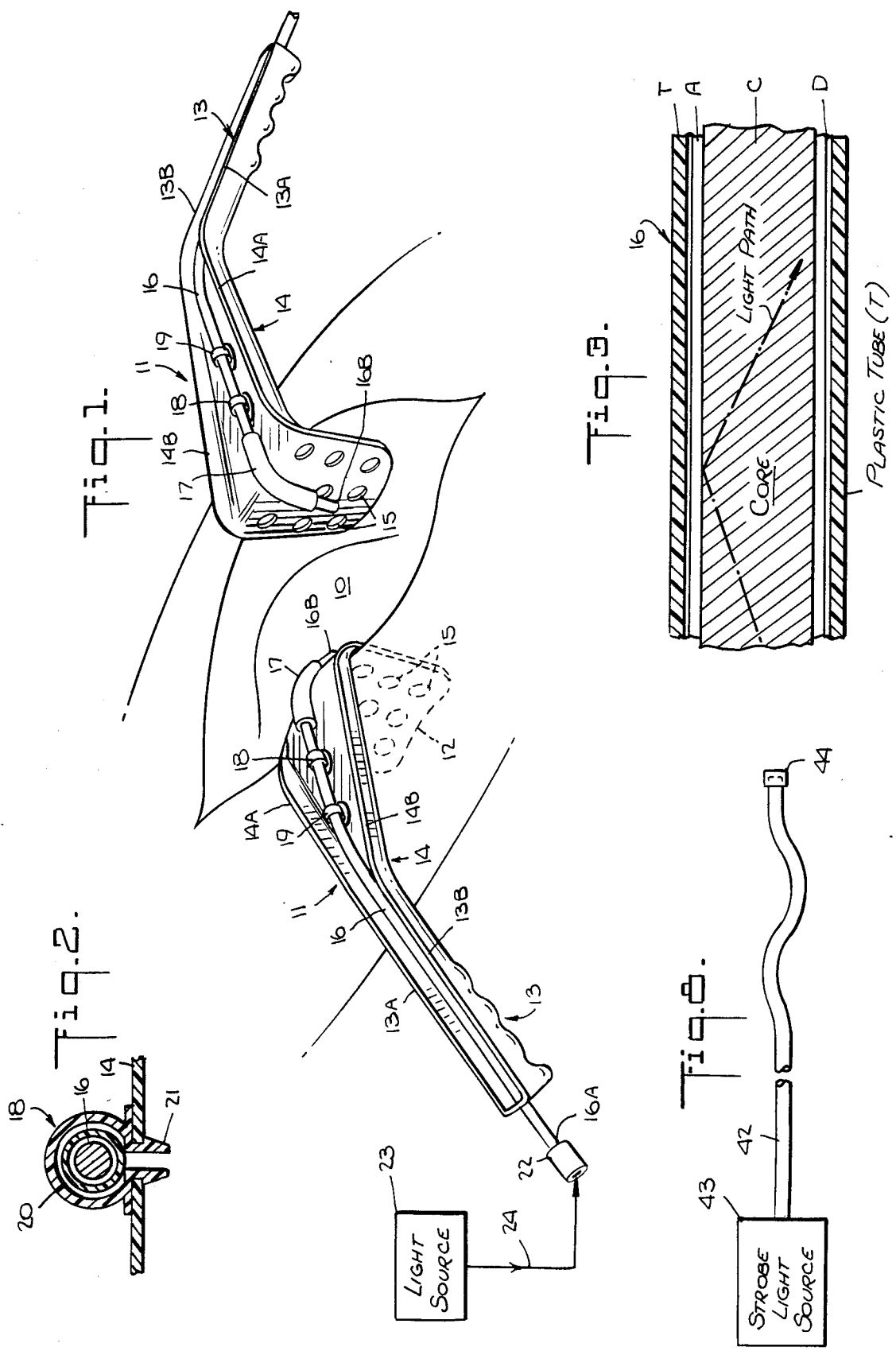

MEDICAL INSTRUMENT AND LIGHT PIPE ILLUMINATION ASSEMBLY

BACKGROUND OF INVENTION

1. Field of Invention

This invention relates generally to medical instruments provided with means to illuminate the field of medical interest, and more particularly to a disposable medical instrument and light pipe illumination assembly fabricated of synthetic plastic material.

Though the invention will be described mainly in the context of medical, surgical and dental applications, it is to be understood that the invention is not limited thereto, for an assembly in accordance with the invention is capable of transmitting light of high intensity by means of a flexible light pipe to remote or inaccessible work sites which are difficult to illuminate by conventional techniques.

The invention, as it relates to improvements in light pipes, is useful in a broad spectrum of industrial applications to carry out such functions as sensing and controlling, as well as general illumination. It is also useful in providing warning or personal safety lights to be mounted on bicycles or other vehicles, or to be worn on the person.

The professional concern of doctors, surgeons and dentists is with body cavities and surgical sites which, unless clearly visible, cannot be properly diagnosed or treated. Existing techniques for illuminating such regions are often inadequate and unsafe, for they either do not succeed in supplying sufficient illumination or they generate excessive amounts of heat which may injure human tissue as well as cause discomfort to the observer. In some instances, commercially available illuminators interfere with medical procedures and also constitute a hazard to both patient and doctor.

The standard operating room illuminator is constituted by batteries of explosion-proof spot lamps and floor lamps, which are capable of being shifted or aimed to suit particular procedures. Such illuminators, which are quite costly, are not only cumbersome, but they fail to afford adequate illumination for deep cavities, in that the light sources are above or behind the surgeons or other operating personnel, whose heads, hands and instruments, as they shift position, often block the light rays.

In recent years, attempts have been made to use long, flexible fiber optics light guides in medical and related applications. Such guides are advantageous in that they furnish "cold light" and segregate the heavy and bulky assembly of lamp, condenser and cooling system from the point of observation. Also, with the development of flexible fiber optic guides with fused ends and plastic casings, sterilization of the instrument is possible.

In its preferred form, the present invention involves a medical instrument associated with a flexible light guide in a monofilament-core pipe format, this representing a particular species of an optical fiber. It is important, therefore, that the distinctions which exist between a conventional multi-fiber optical light pipe or cable and a light pipe having a monofilament-core be clearly understood.

An optical fiber is a dielectric waveguide structure which functions by internal reflection to confine and guide light. It consists of an inner dielectric material, called the core, surrounded by another dielectric material having a smaller refractive index, referred to as the cladding. Currently, all optical fibers in general use have a cylindrical circular cross section.

The amount of light flux which an optical fiber is capable of conveying depends on the cross-sectional diameter of the core; and when there is a need to transmit large amounts of light at a constant level for purposes of illumination, rather than a modulated light signal for purposes of communication, use is usually made of a bunched cluster of optical fibers, each conveying a small amount of light.

Since the present invention is concerned primarily with illumination, it employs in conjunction with a medical or other work instrument a light guide in the form of a flexible pipe having a monofilament-core of large diameter surrounded by a cladding tube. The monofilament core serves the same function as a cluster of small diameter cores, but operates with far greater optical efficiency to transmit large amounts of light with minimal transmission losses, and it also is more bendable than conventional multi-filament core light pipes.

Fiber optic guides may be used as auxiliary illuminators for close diagnostic and surgical operations, as illuminators for direct or indirect ophthalmoscopes, and as specially shaped illumination accessories to classical-designed cystoscopes, proctoscopes, retractors, and various forms of medical, surgical and dental tools.

Despite the obvious advantages of fiber optics for coldlight illumination, their use in the surgical, medical and dental fields has been relatively limited. The reason for this does not lie in any inherent theoretical deficiency, but in the fact that with existing technology, the three basic components of the fiber optics system, when brought together, do not afford sufficient illumination in those situations calling for large amounts of cold light which can be readily directed to selected regions of a body cavity.

But apart from the limitations of existing multi-fiber light pipes is the fact that with heretofore known combinations of light pipes and medical instruments, both the instrument and the light pipe have to be cleaned and sterilized after each use to render them suitable for reuse, for the high costs of these assemblies do not permit their disposal after a single use. Such post-operative processing militates against the practical value of the combination.

Thus in the 1982 brochure entitled "Fiberoptics for Surgery," published by Applied Fiberoptics, Inc., a company affiliated with Codman & Surtleff, Inc., of Randolf, Mass. (Codman), there is illustrated a stainless steel "Britetrac" retractor associated with a fiber optic bundle to deliver cool illumination to the surgical field.

According to the Codman brochure, the "Britetrac" instrument lends itself to processing in ultrasonic washers to avoid tedious hand cleaning. But then the instrument, including the fiber optic bundle, must be sterilized in an autoclave or by other acceptable means.

Another serious limitation of the Codman "Britetrack" instrument is that the light emitted from the outlet of the light pipe is on a fixed axis, and the surgeon, in the course of an operating procedure in which the retractor position remains unchanged, must alter the orientation of the light input in order to better illuminate, say, a deep recess in the surgical site which is not in line with the outlet. While the surgeon could then instruct an assistant to adjust the overhead lights to supply more light to the recess, his assistant may then not be free to make this adjustment; or if he is free, he may not understand what the surgeon has in mind.

A highly significant advantage of the present invention is that the outlet end is readily orientable by the surgeon himself who may redirect the light from time to time toward any region of interest. And because the invention lends itself to combining several light pipes with a single instrument, each pipe outlet may be oriented differently by the surgeon to afford a highly versatile illumination capability.

2. Prior Art

The prior art patent of greatest interest is the Reick-Wilder U.S. Pat. No. 3,641,332, which discloses a flexible light pipe constituted by a monofilament core of resinous material of large diameter, such as methyl methacrylate contained within a cladding tube formed of FEP (Teflon), the core being separated from the tube by a film of air.

As pointed out in this patent, the ideal light guide has a core of the highest possible refractive index in combination with a cladding of the lowest possible refractive index. Commercially-available light pipes, such as the "CROFON" pipe made by duPont, falls far short of this ideal, for this pipe makes use of a polymethyl methacrylate core in a polyethylene cladding tube.

Polyethylene has a refractive index of 1.54, as compared to air, whose index is 1.0. However, though air has the lowest possible refractive index, air normally cannot serve as a cladding, for, if unconfined, it is incapable of protecting the core from scratches and contamination which degrade its quality. In the Reick-Wilder light pipe, one still has a protective plastic outer tube; but it is the inner air film, except at those limited points where the core makes physical contact with the tube, which acts effectively as a cladding having the lowest possible refractive index. At those points where the core touches the Teflon tube, internal reflection will still take place, for Teflon has a refractive index of about 1.34 which is lower than that of the core and therefore functions as a cladding, though this cladding is less effective than air.

Also pertinent to the present invention is the Wilder-Kanbar U.S. Pat. No. 3,729,006, which discloses a hand-held surgical retractors fabricated of light-weight, glare-free, synthetic plastic material.

The Wilder-Kanbar patent spells out the many advantages gained by the use of a plastic retractor over conventional, relatively heavy and expensive stainless steel retractors. But in the context of the present invention, the greatest value of the all-plastic retractor is that it can be combined with an all-plastic light pipe to create a unit that is low-cost and disposable, thereby obviating the need for post-operative cleaning and sterilization procedures. These procedures are time-consuming and require hospital personnel for this purpose. When one considers the total cost of processing a unit so that it can be reused in a surgical procedure, little is lost in discarding the inexpensive, all-plastic unit and using a fresh unit in the next procedure.

SUMMARY OF INVENTION

In view of the foregoing, the primary object of this invention is to provide an improved medical instrument and light pipe illumination assembly which when put to use assumes a position at which its operative section lies adjacent the field of interest, the light pipe functioning to illuminate the field or a selected region thereof.

The significant feature of the invention is that both the instrument and the short light pipe associated therewith are made of low-cost synthetic plastic material whereby the entire assembly is disposable after a single use; and there is no need to clean and resterilize the assembly.

Also an object of the invention is to provide a flexible light pipe of plastic material whose monofilament core is surrounded by a low-cost cladding tube having a thin internal coating formed by a dialetric having a refractive index which is lower than that of the more expensive cladding tubes previously used. Thus the light pipe, though optically more efficient than prior art pipes, is nevertheless substantially less costly.

Still another object of this invention is to provide a flexible light pipe of plastic material having a monofilament resinous core that has impurities uniformly dispersed therein to cause light scattering, thereby degrading the light-transmitting properties of the light pipe, whereby the light is emitted along the pipe rather than at the outlet thereof, and the light pipe therefore glows and serves as a safety or guidance light.

Briefly stated, these objects are attained in the case of a disposable medical instrument and light pipe illumination assembly in which the instrument, such as a surgical retractor, when put to use, assumes a position in which its operative section or blade lies adjacent the field of interest, such as a body cavity or surgical site.

Joined to the instrument by means of routing clips or by routing loops molded therein is a short flexible light pipe whose inlet end is provided with a connector adapted to couple the pipe to a light source, the outlet end being next to the operative section whereby light from the source transmitted through the pipe is projected from the outlet end. The outlet end is sheathed in a bendable tubular neck having dead-soft characteristics whereby the user, by bending the neck, may so orient the outlet as to direct the light projected therefrom to illuminate a desired region in the field of interest.

In a preferred embodiment of the light pipe, the core is a monofilament of resinous material having a relatively high refractive index capable of transmitting light by internal reflection, the core being surrounded by a low-cost flexible tube whose interior cross section is slightly larger than the cross-section of the core to define an annular air film between the tube and the core, the tube having an internal dielectric coating having an exceptionally low refractive index.

OUTLINE OF DRAWINGS

For a better understanding of the invention as well as other objects and further features thereof, reference is made to the following detailed description to be read in conjunction with the accompanying drawings, wherein:

FIG. 1 illustrates, in perspective, a surgical site and a pair of retractor-light pipe illumination assemblies in accordance with the invention in use at the site;

FIG. 2 is a sectional view of a routing clip to hold the light pipe to the retractor;

FIG. 3 is a longitudinal section taken through a light pipe in accordance with the invention;

FIG. 8 is a modified light pipe in accordance with the invention functioning as a glow pipe for safety and warning signal applications.

DESCRIPTION OF INVENTION

The Assembly

Figure 4:
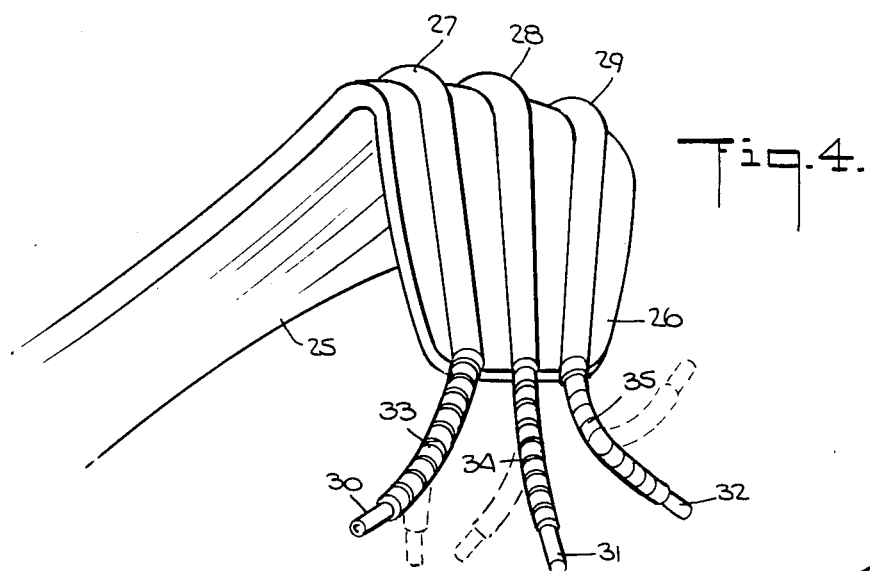
FIG. 4 is a perspective view of another embodiment of a retractor in combination with light pipes to create an assembly.

Referring now to FIG. 1, there is shown a surgical site 10 produced by an incision. Exposure is effected by a pair of retractors 11 and 11', whose blades engage the tissue along opposing walls of the site, the retractors being handled by surgical assistants under the direction of the surgeon.

Each retractor 11 is formed by three components which are integral with each other and are fabricated of a moldable plastic of high-strength, resilient material, such as nylon, polyethylene, or polycarbonates having high impact strength. Polycarbonates have the greatest resistance to deformation under load of any thermoplastic material currently known. The three components are a blade 12, a handle 13, and a shank 14, connecting the handle to the blade. Formed in blade 12 is an array of circular apertures 15. The entire structure may be made by well-known injection molding techniques.

Blade 12 is generally rectangular in form, the lower corners thereof being rounded to avoid sharp edges. The blade is slightly curved inwardly with respect to the tissue engaged thereby, whereby the tissue bellies into the concave inner surface of the blade to make contact therewith throughout the entire area of the blade. Since pulling pressure is applied, small knobs of tissue enter the apertures 15, whose walls are preferably tapered outwardly toward the exterior surface of the blade to permit the knobs to expand somewhat within the aperture. As a consequence, a skid-resistant engagement is effected between the blade and tissue, which prevents slippage or displacement of the blade, even with relatively low pulling pressure. Because the apertures are circular, they are free of sharp corners or discontinuities, and in no way damage delicate tissue.

Shank 14 is at right angles to blade 12, and is provided with raised reinforcing ribs 14A and 14B extending along the longitudinal sides thereof, the ribs at one end merging into the corresponding edges of the blade 12, and at the other end merging into the reinforcing ribs 13A and 13B of handle 13.

The undersurface of handle 13 is corrugated to form a finger grip. The handle is inclined downwardly with respect to shank 14 at an angle comparable to that of a pistol grip. The angular relationship is such that when the handle is grasped by the fingers of the hand, the shank then extends in the horizontal plane above the hand, and the blade lies in the vertical plane, which is the optimum posture for retraction.

Because of reinforcing ribs 13A and 13B, a long channel is formed in the upper surface of the grip, into which one may place the thumb of the hand to thereby maintain the proper orientation of the retractor and resist angular displacement. The outer surface of the plastic is provided with a matte finish to avoid reflectivity.

Joined to each plastic retractor to form an assembly therewith is a short flexible light pipe 16 of plastic material whose inlet end 16A passes through a bore in the end of handle 13, the pipe then extending through the long channel between parallel ribs 13A and 13B of the handle and along the upper surface of shank 14. The outlet end 16B of the plastic light pipe is sheathed in a bendable tubular neck 17 which is curved down over blade 12 of the retractor to function as a light director.

To hold the light pipe to the retractor, at least two snap-in plastic routing clips 18 and 19 are provided at spaced positions and are inserted in bores in the shank of the retractor. Each clip, as shown in FIG. 2, is provided with a retaining loop 20 which encircles the light pipe and a pair of flexible barbed prongs 21 which when inserted in the shank bore, lock the clip thereto. In practice, instead of snap-in routing clips, the loops to retain the light pipe may be molded into the retractor.

The inlet end 16A of the light pipe terminates in an optical connector 22, preferably of plastic material adapted to couple the short light pipe in the assembly to a high-intensity light source 23 by way of a line 24. This line may be a long light pipe of the same type as the short light pipe so that the light source which is electrically powered is at a safe distance from the operating table and beyond the sterile field.

In practice, the light source may be of the type disclosed in the above-identified Reick-Wilder patent, whose entire disclosure is incorporated herein by reference, or of the types being marketed by Codman and illustrated in the above-identified Codman brochure.

The bendable neck 17 is made of thin tubular material, such as aluminum, which has dead-soft characteristics and is altogether without memory, so that when the neck is manually bent and then released, it retains its deformed state without springing back. Hence when the retractor and light pipe assemblies are in use at a surgical site, as shown in FIG. 1, light from the source is transmitted through the light pipes and projected from the outlet ends thereof into the surgical site. Since in the course of a surgical procedure, the surgeon may wish to concentrate the light on a particular region in the site, in order to do so, he has only to bend the light director neck so as to orient the outlet end of the pipe in the desired direction, the neck then acting in a manner comparable to a goose neck. And this bending action of the neck may be carried out repeatedly as other regions require illumination in the course of a procedure.

Because the light pipe and the retractor are both of low-cost, synthetic plastic material, and are sterilized before being packaged, they may in an operating room be put to immediate use. After an operation, the low-cost assembly may be discarded.

The retractor, as shown in FIG. 1, is but one example of a plastic surgical retractor or other medical or dental instrument that is combinable with a short light pipe to define an assembly in accordance with the invention.

In some instances, where the instrument is to be used for a relatively brief period to examine a small body cavity in which relatively little light is necessary to illuminate the cavity, the light pipe inlet may be coupled to a battery-operated light source which in practice could be sealed within the handle of the instrument, so that there is no need to couple the assembly to a remote light source. And in a unit which incorporates a battery-operated light source, the entire assembly may be discarded after a single use to avoid problems of sterility.

The Light Pipe

As shown in FIG. 3, the light pipe 16 used in the assembly is constituted by a flexible core C enclosed in a flexible cladding tube T but separated therefrom by a film of air A, so that the protective properties of a cladding tube are combined with the optical effects of air.

The inner surface tube T is coated with a dielectric oil D of exceptionally low refractive index. Reflections occur at the interface of the core C and air film A, the cladding in this instance serving to strengthen the tube and to protect the core. There is no reflection from the inner surface of the clad in those areas where the clad is separated from the core by an airspace.

Before giving examples of how a light pipe in accordance with the invention is fabricated and the materials used therein, we shall set out in the table below, the refractive indices of certain materials of interest:

| Material | Refractive Index |
| --- | --- |
| Air | 1 |
| Water | 1.333 |
| Teflon FEP | 1.35 |
| CR-39 Alkyl diglycol carbonate | 1.5 |
| Lucite (Polymethylmethacrylate) | 1.49 |
| Polyethylene | 1.54 |

One method of making a light pipe of the type including an air film between the core and cladding tube is to fill an elongated tube of polyethylene having an internal oil coating D with a core of clear catalyzed resin, which may be methyl methacrylate or alkyl diglycol carbonate (CR-39), the core having a cross-sectional area slightly smaller than that of the tube interior to define an annular air space therebetween.

In making the pipe, the selected monomer of core resin in flowable form is first vacuum-filtered and degassed. It is then sucked into the polyethylene tube, which is bent into a U-formation to prevent leakage of the resin. The filled tube is then subjected to heat at an appropriate temperature level and for a period of time sufficient to cure the resin therein. In the course of polymerization, the resin core within the tube shrinks and separates from the tube to create an annular air film between the tube and core.

A resin (CR-39) which is undercatalyzed, remains flexible. Hence by using an undercatalyzed resin as the core material, flexibility of an otherwise rigid core material is obtained; and while this core lacks strength, this is not a problem, for the resin is protectively sheathed by the relatively strong polyethylene.

A light-transmitting pipe of the above-described type has superior light-gathering power because the difference in refractive indices of the core and air sheath are markedly greater than those in existing pipes. The index of polymethylmethacrylate (Lucite) is 1.49 as compared to air, which is 1.0. An even greater difference is had with CR-39, whose refractive index is 1.5.

In those places where the core material touches the oil coating on the outer tube, some light losses occur, but these losses are not substantial, since the coating has a refractive index which is low, depending on its type, this value being lower than the core index. Thus, for the most part, internal reflection in the pipe occurs at the interface of the core and air film, except where the core makes contact with the tube coating and is reflected thereby.

The preferred dielectric oil coating for the polyethylene tube is a perfluoroalkyl-polyether (PFAPE) or a perfluoropolyether (PFPE) sold commercially under the duPont trademark KRYTOX. These have a refractive index which for different grades of these fluorinated oils ranges from 1.300 to 1.301. Also usable is a fluorinated oil sold under the trademark "Fluoroinert" which in different grades has a refractive index of 1.251 to 1.280. Also usable is FOMBLIN having a similar chemistry.

The advantage of using a viscous oil dielectric coated polyethylene cladding tube over a Teflon tube as in the Reick-Wilder patent is that even though a Teflon tube is much more expensive, its refractive index is not as low as that of the oil dielectric; hence it does not combine with high refractive index core to create as efficient a light guide as the core and oil dielectric combination. In the present invention, the polyethylene tube, which is much less expensive than Teflon, serves only as a protective sleeve for the core and its refractive index does not come into play in the optics of the pipe.

Other Assembly Embodiments

Referring now to FIG. 4, there is shown an assembly including a retractor molded of synthetic plastic material and having a shank 25 and a blade 26 about normal thereto, the retractor handle being omitted from the figure.

The retractor is molded to incorporate three parallel tunnels 27, 28 and 29 which run along the shank and down the blade. Threaded through these tunnels are three light pipes 30, 31 and 32 whose outlet ends extend beyond the exits of the tunnels at the edge of the blade. These outlet ends are sheathed in helically-wound bendable necks, 33, 34 and 35 formed of dead-soft strip metal.

The helical construction of the neck facilitates bending thereof without distortion of its tubular form and, as in the case of the retractor shown in FIG. 1, because of the necks, it becomes possible in the course of a surgical procedure to bend them so as to orient the outlets of the light pipes to direct light toward a desired region and to change the direction from time to time.

Figure 5:
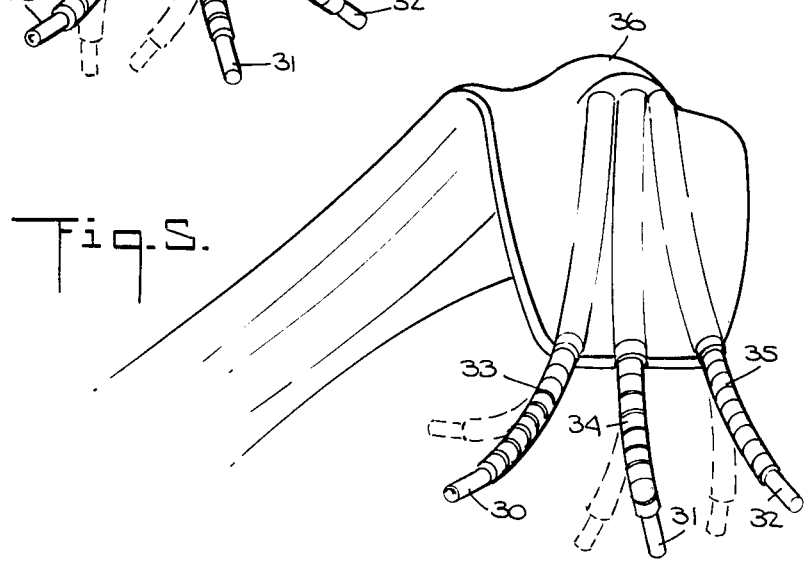
FIG. 5 is a perspective view of still another retractor and light pipe assembly.

The retractor shown in FIG. 5 is similar to that in FIG. 4, except that instead of three parallel tunnels running along the shank to accommodate the three light pipes, there is a common tunnel 36 which serves the same purpose.

As pointed out previously, whenever a medical or dental instrument is to be inserted in a body cavity, such as the mouth, the ear or the vagina, there is invariably a need to illuminate the cavity so that the physician or surgeon can observe the region of interest.

Figure 6:
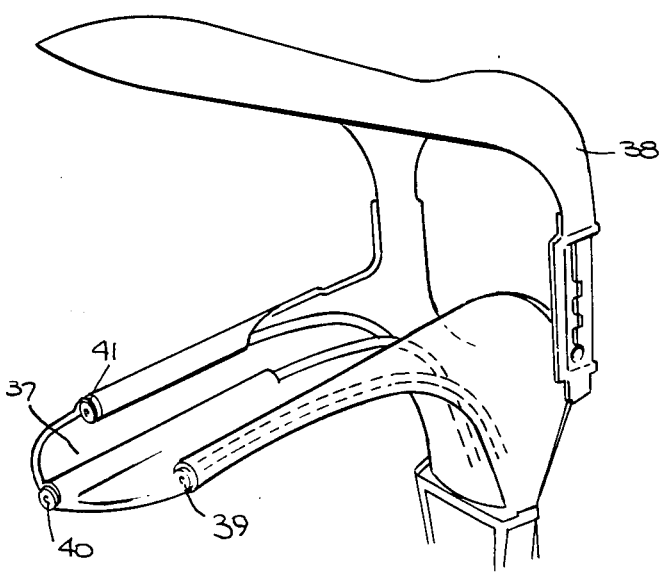
FIG. 6 is a perspective view of a speculum in combination with light pipes to create an assembly.

Thus in a vaginal examination, it is common practice to separate the vaginal lips by means of a speculum. In the embodiment of the assembly shown in FIG. 6, the speculum, which is fabricated of synthetic plastic material and is therefore disposable, includes a fixed lower jaw 37 and a movable upper jaw 38 which is shiftable from an initial closed position in which it lies against the lower jaw to facilitate insertion in the vagina between the lips thereof, to a raised operative position which acts to separate and hold open the lips and thereby permit vaginal examination.

In this arrangement, the lower jaw 37 is provided with three parallel light pipes 39, 40 and 41 to illuminate all regions of the vagina, these pipes running through spaced tunnels molded in the lower jaw. While bendable necks are not shown in FIG. 6, in practice, these may be added to the pipe outlets to render them orientable.

While these light pipes in the speculum assembly may be coupled to an external light source, in practice this source is preferably in the form of a miniature battery and high intensity bulb housed in the handle of the speculum. The battery is preferably of the high capacity lithium type.

Abdominal operating procedures are complicated by the fact that the intestinal tubes which are looped in the abdominal cavity block the field of interest, and it is necessary, therefore, to use a self-retaining abdominal retractor system in which several metal retractor blades are adjustably mounted on a ring so as to engage the intestines and create an opening to expose the surgical site. One such abdominal retractor system is the "Bookwalter" system marketed by Codman which provides the surgeon with a versatile system for multi-directional exposure.

Apart from the fact that existing abdominal retractors are mechanically quite complicated and costly, as well as being difficult to adjust, is that they are also troublesome to clean and then resterilize. Moreover, whatever light is available to the surgeon is derived from an overhead lighting system; and, as explained previously, the head of the surgeon working over the surgical site may more or less block this light.

Figure 7:
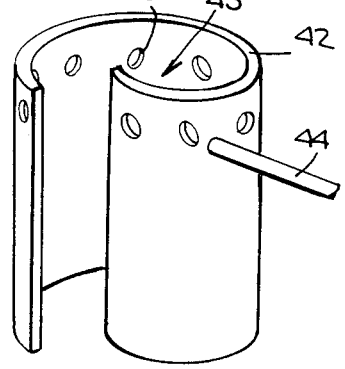
FIG. 7 is a self-retaining abdominal retractor in combination with a light pipe.

In the abdominal retractor shown in FIG. 7, use is made of a flat rectangular panel 42 of flexible synthetic plastic material having the resilient properties of a flat spring, such as is used in spring-wound motors. Suitable for this purpose is "Lexan," a thermoplastic carbonate-linked polymer having a strong memory.

By first coiling this Lexan panel to form a coil column and inserting the column into the looped intestines so as to clear a passage therethrough, and then releasing the coil column, the resultant partially uncoiled panel then bears against the intestines which resists further uncoiling to create an opening 45 exposing the surgical site.

By providing a series of holes 43 along the upper margin of the panel, one may, after the partially uncoiled retractor is in place, then insert a light pipe 44 through one of the holes to spill light into opening 45 to illuminate the surgical site. Alternatively, a light pipe with a tubular light director neck of dead-soft material may be clipped onto the panel.

Safety Glow Pipe

There are many situations which require a safety light to call attention to a vehicle or to a person under conditions where it is difficult to otherwise see the vehicle or person. Thus a child riding a bicycle at dusk or at night on a road also used by motor vehicles is in danger of being run down, and this is also true of a jogger on the same road.

The use of a rear reflector on a bicycle is a commonplace safety measure, but somewhat ineffective; for a driver in an automobile behind the bicycle does not see the reflector until it picks up light from the car headlights, and that may be too late to avoid a collision. And a waist belt on a jogger which carries reflectors is similarly ineffective.

While it is possible, because of its flexibility, to attach a light pipe to the frame of a bicycle or around the waist of a jogger, a light pipe of the type previously described because of its inherent light transmission characteristics would be no better than a light bulb; for almost all light from the light source coupled to the inlet of the pipe would pour out of the pipe outlet, whereas the length of the pipe would be dimly lit.

In order to convert the optically efficient light pipe previously disclosed in the Wilder-Reick patent or of the modified type in which the translucent cladding tube has an inner dielectric liner of low refractive index into a glow pipe in which light is emitted along the full length of the tube and virtually no light reaches the outlet, impurities are introduced into the monofilament resinous core. These impurities act to scatter the light being transmitted and therefore interfere with the normal fiber optics internal-reflection properties of the pipe.

A suitable impurity for this purpose is titanium dioxide, fine particles thereof being uniformly dispersed in the monomer of the flowable core resin before this monomer is used to fill the cladding tube and polymerized in the manner previously described. Thus the particles are embedded in the core.

Thus in the glow pipe, light fed into the inlet is transmitted by internal reflection through the pipe and in the course of transmission is scattered by the impurities, the scattered light causing the pipe to glow along its full length. The glow tube therefore behaves as a lossy or inefficient light transmitter.

As shown in FIG. 8, in order to make possible prolonged operation of glow pipe 42 in circumstances where a power line for energizing a light source is not available or feasible, use is made of a miniaturized strobe light source 43 which is battery operated. A strobe light source emits periodic flashes of high intensity light of extremely short duration, separated by relatively long relaxation intervals whose length can be as long as a half second, so that the duty cycle is low and very little power is consumed. In this way, even a small capacity battery is capable of operating a strobe light for several hours, and a larger battery for several days, if not longer. A glow pipe which flashes intermittently is more effective as a safety signal than one which has a constant light level, for a flashing light attracts more attention than a fixed light.

In practice, the outlet of glow pipe 42 may be terminated by a reflective cap 44 so that whatever light reaches the outlet is returned toward the inlet to cause the pipe to glow more or less uniformly along its length. Because the glow pipe is flexible, it may be linked to a bicycle frame to illuminate any desired portion thereof, the strobe light box being strapped to the frame at a convenient position thereon.

And in the case of a jogger or other individual who requires a safety signal light, the glow pipe may be configured to create a waist band and even a head band. Also, the glow pipe can be combined with a safety helmet or other article of apparel. And the glow pipe may even be made in the form of a skipping rope.

The glow pipe can be made in long lengths to serve as a directional signal line along a circuitous walkway, as in an airport terminal, with the light being colored to indicate that by following, say, the red line, one will reach a given destination, and by following a green line, one will reach another destination.

And because of its flexibility, the plastic glow pipe can be configured to create decorative patterns, symbols or signs very much in the fashion of a neon tube sign, but without the need to bend glass tubing. Thus in an emergency, one could quickly erect a glow pipe sign.

While there have been shown and described preferred embodiments of a medical instrument and light pipe illumination assembly in accordance with the invention, it will be appreciated that many changes and modifications may be made therein without, however, departing from the essential spirit thereof. Thus in the case of the abdominal retractor instead of a coiled panel to create a space in the abdomen, one may use a complementary pair or group of retractors whose blades, when together, create a tongue for insertion into the site, a snap spring cooperating with the retractors to cause them to separate after insertion to form the desired passage to the operating site.

The glow pipe disclosed herein also has medical applications, for it can be formed into a ring to surround a surgical site to afford omnidirectional illumination.

Finally, it must be noted that the overriding advantage of a disposable retractor and light pipe assembly in accordance with the invention and the reason it is of significant value to the operating surgeon having the benefit thereof, is that it puts in the hands of the surgeon full control at the operating site of the illumination vital to the success of the procedure. The surgeon has no need to move beyond the operating site in order to redirect the illumination as is often necessary in a difficult procedure. The fact that the surgeon can confine his efforts and concentrate his attention to the operating site is of benefit to the patient, for any action taking the surgeon away from the operating site may endanger the patient.

In the dental field, a short light pipe having an orientable outlet in accordance with the invention may be combined with a synthetic plastic suction tube to remove liquid from the oral cavity rather than the metal tube presently used for this purpose, to provide a disposable assembly which affords the dentist a source of illumination which he can manually direct as required. Or the orientable light pipe can be combined with a dental mirror or other dental appliance.

In the glow pipe previously disclosed, in lieu of titanium dioxide particles as the light scattering agent, one may use spheroidal, fine particles of transparent polyethylene whose basic density is about the same as that of the methyl methacrylate core, but whose refractive index is slightly different, these particles being uniformly dispersed in the core to render it optically lossy.

In the abdominal retractors previously disclosed, in which use is made of a flexible panel or band of Lexan, there is a need to maintain the operative configuration of the retractor which is assumed after the coiled band has been inserted into the abdominal cavity and released, whereby the uncoiled band then creates an opening exposing the surgical site. This can be accomplished by providing the Lexan band with a tongue projecting from the center of the band at one end thereof. The band is also provided with a series of equispaced slots running along its longitudinal center line. These slots are adapted to receive the tongue which is inserted in that slot presented to the tongue when the band is more or less uncoiled.

Also, in this abdominal retractor, a strip of nonwoven soft fabric matting material may be bonded to rear surface of the Lexan band to cushion the retractor within the surgical site. The holes in the top of the Lexan band for receiving the outlet end of the light pipe associated with the retractor may be in key hole or in otherwise slotted form, making it possible to laterally snap the pipe outlet into the hole.

While in the foregoing specification the advantages of using a disposable plastic retractor in combination with a plastic light pipe have been stressed, in some instances, it may be desirable to combine the light pipe having an orientable outlet with a standard non-disposable metal surgical retractor. To this end, use may be made of a light pipe adaptor in the form of a strip of resilient plastic material having a width more or less matching the length of the blade of the standard retractor, and having an entry slot therein at the midpoint of the strip through which one may insert the retractor blade so, that the strip is then behind the rear of the blade and held thereto, the strip extending outwardly from either side of the blade. The rear of the strip may have a cushioning fabric laminated thereto, for it is this rear which is pressed against the tissue wall of the surgical site when the retractor is put to use.

Above the entry slot in the strip is a key hole in line with the handle of the retractor into which one may snap in the orientable outlet of the light pipe. In gripping the retractor by its handle, the operator may, at the same time, hold the light pipe extending along the handle within his grip.

We claim:

1. A disposable medical instrument and light pipe assembly comprising:
   A. an instrument molded of synthetic plastic material and provided with an operative section which, when the instrument is used, lies adjacent the field of interest;
   B. a short, flexible light-transmitting pipe joined to the instrument, the pipe having a core surrounded by a cladding tube, both formed of synthetic plastic material, said pipe having an optical inlet end adapted to be coupled to a light source and an outlet end next to said operative section to project light transmitted through the pipe toward the field of interest; and
   C. a bendable tubular neck of dead-soft material ensheathing the outlet end to render it orientable, the material being without memory so that when the neck is manually bent and then released, it retains its deformed state without springing back, whereby by bending the neck the user without changing the position of the instrument can direct and redirect light from the outlet toward a desired region in the field.

2. An assembly as set forth in claim 1, wherein said tubular neck is formed by a flat metal strip helix.

3. An assembly as set forth in claim 1, wherein said instrument is a retractor having a handle, a shank extending from the handle, and a blade extending from the shank and serving as the operative section, the light pipe joined to the retractor running along the handle and shank to the operative section.

4. As assembly as set forth in claim 1, wherein said instrument is a speculum having a fixed jaw and a movable jaw, said light pipe being joined to said fixed jaw.

5. An assembly as set forth in claim 4, wherein said speculum is provided with a handle which incorporates a battery-operated light source coupled to the outlet of the pipe.

* * * * *